Figure 1:
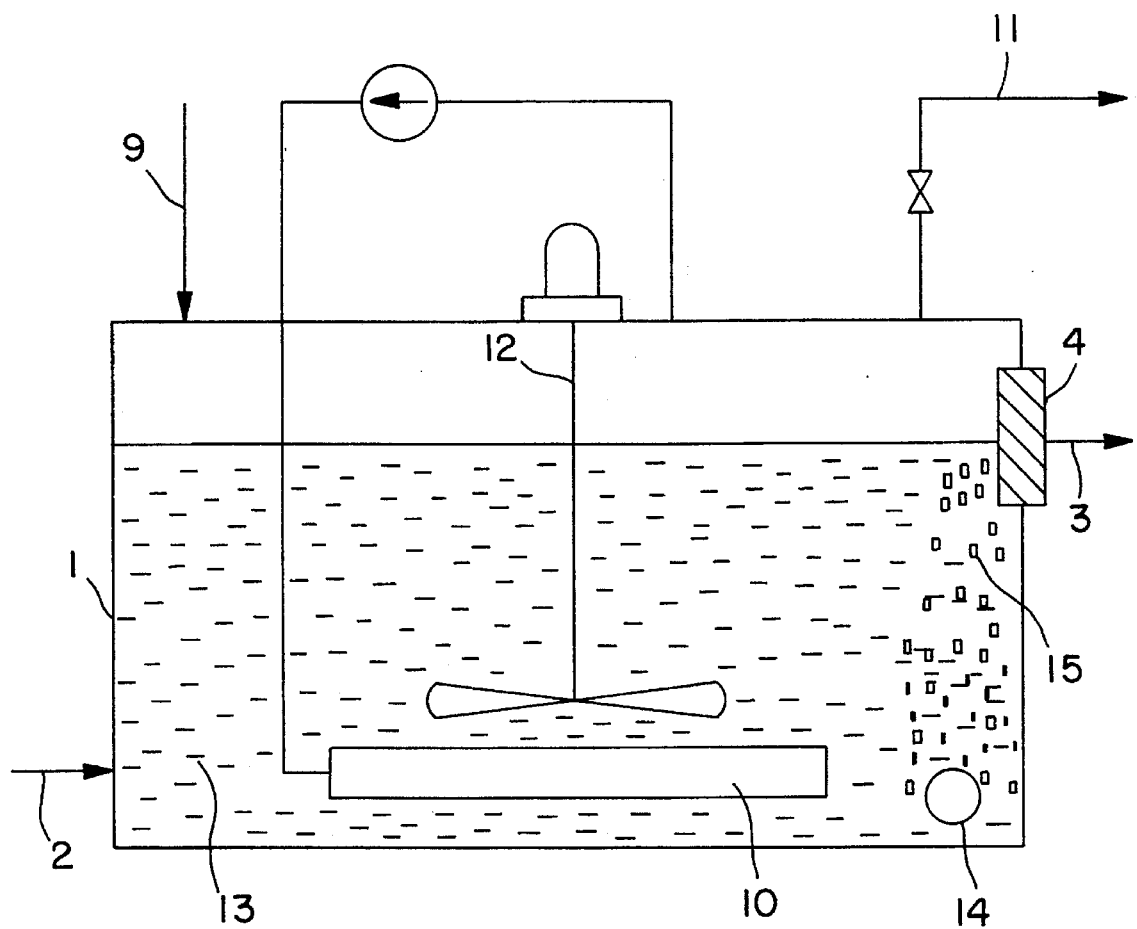

United States Patent [19]
Fuchs

[11] Patent Number: 5,618,430
[45] Date of Patent: Apr. 8, 1997

[54] PROCESS FOR PERFORMING REACTIONS

[75] Inventor: Uwe Fuchs, Munich, Germany

[73] Assignee: Linde Aktiengesellschaft, Wiesbaden, Germany

[21] Appl. No.: 290,898

[22] PCT Filed: Feb. 19, 1993

[86] PCT No.: PCT/EP93/00403

§ 371 Date: Feb. 23, 1995

§ 102(e) Date: Feb. 23, 1995

[87] PCT Pub. No.: WO93/16792

PCT Pub. Date: Sep. 2, 1993

[30] Foreign Application Priority Data

Feb. 24, 1992 [DE] Germany .......................... 42 05 572.5

[51] Int. Cl.$^6$ ................... B01J 2/28; C02F 1/28; C02F 3/08
[52] U.S. Cl. .................. 210/616; 210/763; 210/807; 95/36; 423/DIG. 16
[58] Field of Search ..................... 210/616, 762, 210/763, 749, 807, 150, 151, 661, 205, 694, 617; 95/36, 275; 423/DIG. 16, 230

[56] References Cited

U.S. PATENT DOCUMENTS 3,998,988  12/1976  Shimomai et al. ................... 428/400
4,664,803   5/1987  Fuchs et al. ......................... 210/616
4,759,922   7/1988  Perrone ............................... 423/597
4,876,288  10/1989  Herding et al. ..................... 210/616
5,009,790   4/1991  Bustamante et al. ................ 210/689
5,403,487   4/1994  Lodaya et al. ...................... 210/616

*Primary Examiner*—Thomas G. Wyse
*Attorney, Agent, or Firm*—Millen, White, Zelano, & Branigan, P.C.

[57] ABSTRACT

The invention relates to a process for performing chemical and/or physical and/or biological reactions, in which the reactants are brought into operative connection with reaction particles 13 promoting or making possible the reaction. The invention furthermore relates to reaction particles 13 as such. It is proposed to use as reaction particles 13 essentially planar particles with a thickness of about 5 μm to about 1500 μm and an area of about 5 (mm)$^2$ to about 1000 (mm)$^2$. Reaction particles 13 can be used, e.g., as growth surface for biomass. In particular, they can be introduced in a wastewater reactor 1 and thoroughly mixed with the waste water. Reaction particles 13 have a very high specific surface, which, moreover, is easily accessible. Furthermore, reaction particles 13 can be easily set in motion, e.g., by a stirrer 12.

20 Claims, 3 Drawing Sheets

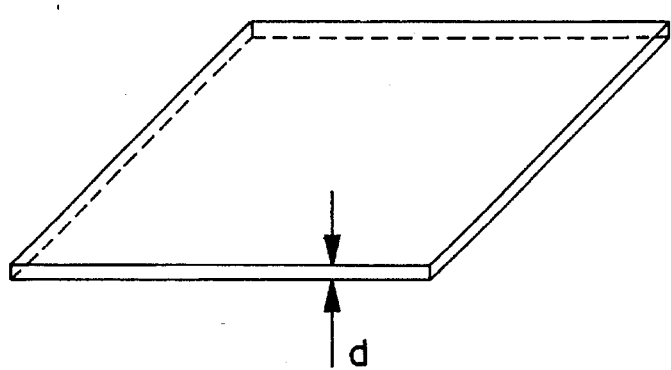
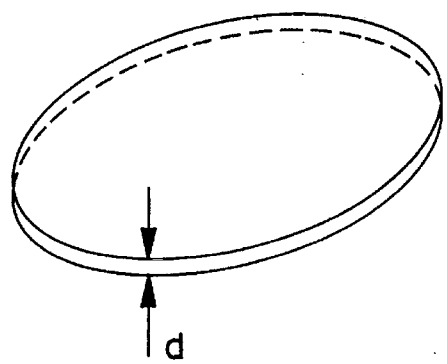
FIG. 2a
FIG. 2b
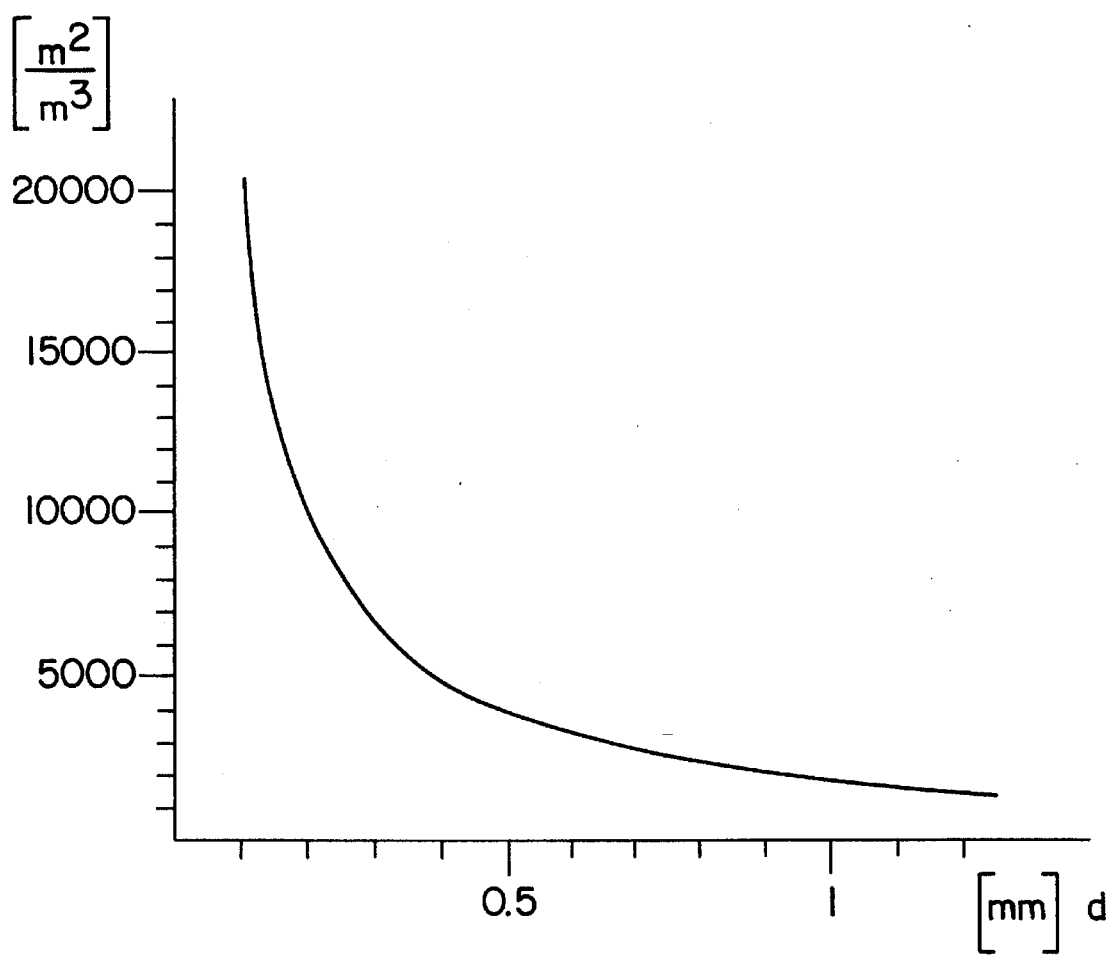
FIG. 3

PROCESS FOR PERFORMING REACTIONS

DESCRIPTION

The invention relates to a process for performing chemical and/or physical and/or biological reactions, in which the reactants are brought into operative connection with the reaction particles promoting the reaction or making it possible.

In process engineering, in many cases, chemical, physical or biological reactions are performed in the presence of reaction particles, which either have a catalytic effect, i.e., promote a certain reaction between the reactants, or themselves act as reactants, i.e., themselves go into a reaction with another reactant. Thus, carrier particles are used, for example, in waste-water engineering as growth surface for microorganisms. The carrier particles overgrown with biomass act as biocatalysts and promote the degradation of materials contained in waste water. It is also known to dope the carrier particles with activated carbon, so that the carrier particles react physically based on the adsorptive effect of the activated carbon itself with the materials contained in the waste water. The use of catalyst materials or carrier particles for biomass is also known from the physicochemical or biological waste-gas treatment. Also, in fermentation processes in biotechnology, carrier particles are also used as growth surfaces for biomass.

In standard fluidized-bed or suspended-bed reactors for waste-water or waste-gas treatment, above all sand, gravel, expanded clay, plastic granules or foam cubes are used as carrier particles. These carrier particles all exhibit a spatial structure and thus cause a certain dead volume in the reactor. In the porous carriers, moreover, materials transport problems may occur, so that only the outer carrier surface is intended as growth surface for the biomass by many experts and engineers. Furthermore, the known reaction particles exhibit only a small specific surface. The specific weight of the particles is often too great (e.g., in the case of sand) or too small (e.g., in the case of styropor foam). The mechanical and/or chemical durability, moveover, often leaves something to be desired. High material costs often do not allow an economical use of the carrier particles. Some materials are, moreover, not allowed, e.g., for drinking water treatment, for physiological reasons.

The object of this invention is therefore to make available an economical process for performing chemical and/or physical and/or biological reactions.

This object is achieved according to the invention in that as reaction particles, essentially planar particles with a thickness of about 5 µm to about 1500 µm and an area of about 5 $(mm)^2$ to about 1000 $(mm)^2$ are used.

In accordance with a process aspect, the invention provides a process for treating drinking water or waste water and/or waste gas, in which the drinking water or waste water and/or waste gas is brought into contact with reaction particles that promote the treatment or make it possible, characterized in that as reaction particles, essentially planar particles with a thickness of about 5 µm to about 1500 µm and an area of about 5 $(mm)^2$ to about 1000 $(mm)^2$ are used, which are brought into suspension and/or set in motion in a reactor.

Preferably reaction particles with a thickness of about 15 µm to about 500 µm, especially preferably of about 25 µm to about 150 µm, are used.

By the planar structure, a high specific colonization area and/or reaction area is achieved, which, moreover—in contrast to porous materials—is freely accessible. The specific weight of these confetti-like particles is freely selectable depending on material or material combination, so that the particles in the reactor can be easily fluidized without great energy expenditure and, if necessary, can be easily pumped. If the reaction particles are to be used in a reactor filled with liquid, the specific weight of the particles is preferably adjusted so that it corresponds approximately to that of the liquid. With use in reactors for waste-water treatment, reaction particles are preferably used, whose specific weight is about 0.85 to about 0.95. After these reaction particles have covered themselves with biomass during a starting phase, they have a specific weight of about 1, so that they are suspended freely movable in the waste water and can be set in motion with extremely low energy expenditure, by which the economic efficiency of the waste-water treatment is increased. When using the reaction particles in a process for biological waste-water treatment, biological waste-gas treatment, fermentation or in general, a process from biotechnology, a very active biofilm appears on the reaction particles, which is constantly regenerated. In this way, the treatment efficiency or product yield can be increased significantly relative to usual processes.

But the process according to the invention is suitable not only for such purposes, in which a biological overgrowth of the reaction particles is important. The reaction particles as such can also be used to perform reactions. In this case, the material of the reaction particles is suitably selected so that the desired reactions take place on the surface of the reaction particles. In this case, the reaction particles can act as catalysts, which accelerate the reactions between the reactants or else react on their own with the reactants.

For example, the reaction particles can consist of metal foils, in which the metals used can get the desired reactions going. An example for this is the removal of nitrate from drinking water. In this case, the drinking water is thoroughly mixed with the reaction particles, e.g., in a reactor. The reaction particles consist of pieces of aluminum foil. Under certain conditions, the light metal reduces the nitrate mainly to gaseous nitrogen. The reaction is most effective at pHs between 9.1 and 9.3.

Another possibility consists in using reaction particles, which are doped with reactive substances. Examples for this are the doping with zeolite powder (e.g., for removal of ammonium, nitrate or CKW from ground water) or with iron (e.g., for removal of residual phosphate). Also, the doping with adsorption agents, such as activated carbon, offers advantages in certain applications.

The reaction particles can be made of plastic that exhibit a specific weight of about 0.8 $g/cm^3$ to about 1.5 $g/cm^3$.

According to an especially preferred embodiment of the invention, essentially planar reaction particles are used, whose surface, in addition, is structured. In particular, such reaction particles are advantageous that exhibit holes with a diameter of about 10 to about 1000 holes/$cm^2$, for example, 10 µm to about 1000 µm, preferably 200 to 600 µm. The hole density is suitably about 100 to about 250 holes/$cm^2$. Such reaction particles are produced from plastic films, which are cut into pieces with an area from about 5 $(mm)^2$ to about 1000 $(mm)^2$ each.

Also, embossings of the reaction particles have proven advantageous for the efficiency of the process. In particular, dents with a diameter of about 10 µm to about 1000 µm and a depth of up to about 0.5 mm are preferred. The desired reaction particles with the advantageous properties can also be produced by etching or roughening the film surface.

In biological processes, e.g., in waste-water or waste-gas treatment or in fermentation processes, reaction particles made of polymer compounds are preferably used, which have undergone a surface treatment. In particular, the so-called corona treatment is suitable for this purpose. In this case, there is an electric discharge, in which ozone is released, which again attacks the matrix of the particle material and creates free valences. In this way, the electrical properties of the particle surface are changed, so that the microorganisms can settle more easily on the surface.

A further development of the process provides for using such reaction particles, on whose surface fibers were applied, e.g., by lamination or fleecing, and/or powders were applied. A nonwoven fabric can also be bonded or welded. Fine polyester or polyolefin threads are preferably applied to the surface. In this case, the layer thickness of such coated reaction particles is at most about 0.5 mm to about 1 mm. The coating can take place on one or both sides. The basic material of the reaction particles used itself consists preferably of polyolefins, especially polypropylene or polyethylene. These materials are very inexpensive and have a very advantageous specific weight of about 0.85 to 0.95 g/cm$^3$. After the overgrowth with biomass, there is a specific weight around 1, so that these reaction particles are suspended in aqueous solutions, e.g., in waste water, in the overgrown state. Therefore, extremely little energy is necessary to set the reaction particles in motion. This has a positive effect especially on the economic efficiency of the waste-water treatment processes. Polystyrene is also suitable as basic material for the reaction particles. The reaction particles can be made of easily biodegradable bioplastics.

According to a further development of the inventive idea, reaction particles made of plastic fabric, especially heat-set plastic fabric in knitted form, are used. These fabrics are essentially planar, but already have a specific surface structure, by which the desired reactions and the growth of microorganisms are additionally accelerated.

Suitably, the process according to the invention is performed in reactors. In particular, the process is provided for waste-water and/or waste-gas treatment. For this purpose, the reaction particles in the reactor are brought into contact with the waste water and/or waste gas. In this case, the waste water and/or waste gas is preferably conducted through a stationary bed of the reaction particles. In the waste-water treatment, the reaction particles can also be used for filtration. Another variant of the invention provides for conducting the waste water and/or waste gas through a fluidized bed of the reaction particles. In this case, the bed is broken up and to a certain extent brought into suspension by the waste water and/or waste gas conducted through it. If the invention is to be used for waste-water treatment, the so-called fluidized-bed principle is especially preferred. Accordingly, the reaction particles in a fluidized-bed reactor are completely and thoroughly mixed with the waste water. In this way, an especially effective exchange of materials between the materials contained in the waste water and the reaction particles and a problem-free operation, viewed from the flow, is achieved. The particles are retained in the reactor by screens or gravitational forces.

The process is equally suitable for the anaerobic as well as aerobic biological waste-water treatment. In the aerobic waste-water treatment, an aeration with pure-oxygen is advisable to make up for the very high depletion of dissolved oxygen.

The process can be used especially for nitrification and/or denitrification of waste water. But it is also suitable for main or residual carbon degradation. With the process according to the invention, nitrification, denitrification and carbon degradation can also be performed simultaneously. The process is suitable equally for drinking-water and industrial-water treatment.

In the biological waste-gas treatment, the waste gas is conducted either directly through a moist bed or a fluidized bed of the reaction particles, or the waste gas is first subjected to a scrubbing and then the wash water laden with the materials contained in the waste gas is treated in a reactor filled with the reaction particles corresponding to the carrier-bound waste-water treatment.

If the process is used in biological processes, such as biological waste-water or waste-gas treatment or fermentation, a reactive biofilm forms on the surface of the reaction particles during the starting phase. In this case, the pollutants present in the waste water or waste gas act as nutrients for the microorganisms. To accelerate the starting process or to treat special waste waters or waste gases, it is provided, according to a further development of the invention, to inoculate the reaction particles with special microorganisms. In this case, especially those reaction particles are suitable whose surface condition was changed by the above-described treatment methods, so that even very slowly growing microorganisms, which are suitable for the degradation of unusual materials contained in waste water or waste gas, can settle.

Since the reaction particles used according to the invention have a very much greater specific surface than the carrier particles conventionally used in the carrier-bound biological waste-water and/or waste-gas treatment, a lower filling level of the reactor is sufficient to achieve the same treatment performance. About 3% by volume of the reaction particles according to the invention with a thickness of 0.2 mm produces a reactor-specific surface of 300 m$^2$/m$^3$ of reactor. Preferably, the reactor filling is adjusted, so that the ratio of installed growth area to reactor volume is about 50 m$^2$/m$^3$ to about 2000 m$^2$/m$^3$.

In addition to the process for performing chemical and/or physical and/or biological reactions, the invention also relates to the reaction particles themselves. According to the invention, these reaction particles are distinguished in that they exhibit an essentially planar shape with a thickness of about 5 µm to about 1500 µm and an area of about 5 (mm)$^2$ to about 1000 (mm)$^2$.

Further configurations of the reaction particles are indicated in the subclaims relating to the reaction particles and have already been described in detail above in connection with the process according to the invention, in which the reaction particles are used.

The process according to the invention and the reaction particles according to the invention can be used to perform the most varied reactions. In this case, the reaction particles themselves can be produced from a reactive material, which initiate certain reactions. Especially advantageous is the use of the reaction particles for waste-water, drinking-water or waste-gas treatment. Here, the reaction particles themselves, on the one hand, can produce the desired reactions, e.g., nitrate can be removed from the drinking water by aluminum foils or PHB foils. On the other hand, the reaction particles can be doped with reactive substances (e.g., iron), which, on their part, can get the reactions going. The use of reaction particles in the carrier-bound waste-water and/or waste-gas treatment can be considered as especially very promising. In this case, an especially active biofilm settles on the reaction particles, so that high treatment performances can be achieved.

The invention offers significant advantages relative to the prior art. The high specific surface of the reaction particles allows, for example, a very high treatment performance per reactor volume in a waste-water reactor. The small, light reaction particles are suspended in the water and can be pumped or moved into the reactor with extremely low energy expenditure. The material for the reaction particles can be freely selected with respect to the desired specific weight, durability and physiological harmlessness. Furthermore, the process according to the invention is extremely economical, since the reaction particles can be produced inexpensively. For example, the reaction particles can be produced from plastic wastes or recycling material.

Figure 4:
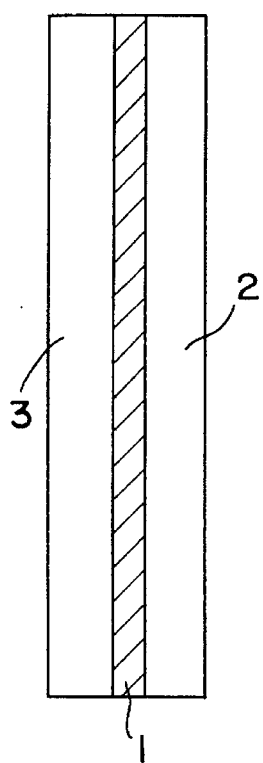
Figure 5:
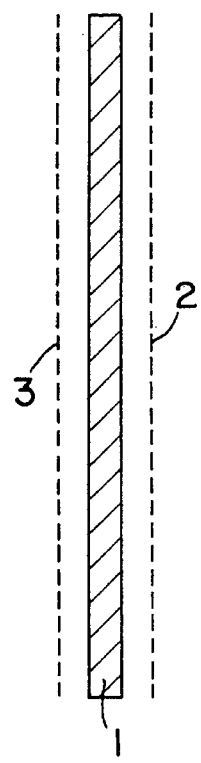
Figure 6:
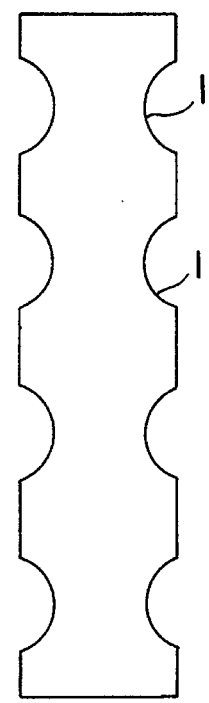

The invention is explained below in more detail based on embodiments diagrammatically represented in the figures:

There are shown in:

FIG. 1: a flow chart of a process for biological waste-water treatment with the reaction particles as growth surface for biomass FIGS. 2A and 2B: sketches of a reaction particle in square and round shape FIG. 3: a diagram of the specific surface of the reaction particles as a function of the thickness of the reaction particles FIG. 4: a cross section of a reaction particle produced from a composite film FIG. 5: a cross section of a reaction particle with pressed-in substrate FIG. 6: a cross section of a reaction particle with dents on the surface.

In FIG. 1, a reactor closed against the atmosphere and designed as a completely and thoroughly mixed activated sludge basin is designated with 1. As indicated by hatching 13, planar particles, as carrier material for the microorganisms, with a thickness of about 200 μm to about 500 μm and an area of about 100 (mm)$^2$ to about 500 (mm)$^2$ are arranged freely movable in activated sludge basin 1 in an amount that corresponds to an installed growth area of about 500 to about 1000 m$^2$/m$^3$ reactor volume. The reaction particles consist of a perforated polypropylene film, about 30 μm thick in the original state, with a hole density of about 200 holes/cm$^2$. The holes exhibit a diameter of about 200 to about 600 μm. The film was subjected to a surface treatment, a so-called corona treatment. The ozone resulting in this case attacks the matrix of the film and creates free valences, by which the electrical surface condition is changed. The microorganisms can settle especially quickly on the thus treated film.

The waste water to be treated is introduced by a feed 2 in activated sludge basin 1, while the treated waste water is drawn off by an outlet 3 connected in the upper area of activated sludge basin 1 to which a separating device 4 for retaining the individual material particles, which can be, for example, a simple screen. For oxygen supply of the microorganisms, a provision is made to supply technically pure oxygen or at least a gas containing more oxygen than air to the gas chamber, designed under the covering of activated sludge basin 2, by a feed pipe 9, and to supply the gas present in the gas chamber by a pipe to a gas distributor 10 arranged near the bottom of activated sludge basin 1. Waste gas is drawn off by a valve-controlled waste-gas pipe 11. The rising gas bubbles of the aerating gas in this case generate sufficient buoyancy to set in motion reaction particles 13, laden with biomass, whose specific weight in the overgrown state corresponds approximately to that of water.

To achieve as good a through mixing as possible and a good material conversion, a circulating device 12, for example consisting of a simple stirring device with electric power drive, is placed directly above gas distributor 10.

In addition to the arrangement, shown in the figure, of feed pipe 9 for treatment gas, the possibility also exists to connect a gas feed pipe directly to the bottom of activated sludge basin 1 by several connections and in this way to generate an additional gas flow directed upward. Waste-water feed 2 can also exhibit several connections distributed over the bottom of the basin also to maintain a liquid flow directed upward in the activated sludge basin.

To keep separating device 4 free, a deep aerating device 14, arranged directly in front of separating device 4, is provided, which creates a high flow rate, directed upward, of about 0.5 m/s. Furthermore, spherical scouring elements 15, especially foam cubes, are added to reactor 1 in an amount of about 1 to 10% by volume. Scouring elements 15, swept along upward with the waste-water flow, rub against separating device 4 and clean settled solids or reaction particles from the latter. The small and light reaction particles can be pumped with extremely low energy expenditure.

Numerical data for a design example of a nitrification unit operated according to the process of the invention in comparison to a usual carrier material unit are indicated in the table below.

|  | Carrier-bound Processes | |
| --- | --- | --- |
|  | usual carrier processes | with the reaction particles according to the invention as carrier particles |
| Amount of waste-water feed (m$^3$/d) | 20,000 | 20,000 |
| NH$^+_4$-N-feed [mg N/l] | 50 | 50 |
| NH$_4$N-outflow [mg N/l] | <10 | <1 |
| permissible nitrogen-surface loading [g N/m$^2$ d] | 2 | 2.5 |
| biosurface to be installed [m$^2$] | 400,000 | 400,000 |
| required film surface [m$^2$] | — | 200,000 |
| film material | — | polypropylene corona-treated |
| film thickness (originally) [μm] | — | 30 |
| perforated film thickness [μm] | — | 300 |
| particle size [mm$^2$] | — | about 200 |
| hole diameter [μm] | — | 200 . . . 400 |
| hole density [Lö/cm$^2$] | — | 100 . . . 200 |
| specific surface relative to compact material [m$^2$/m$^3$] | 250 | about 7000 |
| specific surface relative to reactor volume [m$^2$/m$^3$R] | 175 | 525 |
| carrier density in the reactor [Vol-%] | 70 | 7.5 |
| reactor volumes [m$^3$] | 2500 | 800 |
| costs for carrier material [Mio DM] | 0.6 | 0.1 |
| total investment costs for the reactor [Mio DM] | 1.85 | 0.6 |

FIGS. 2A and 2B show sketches of a reaction particle according to the invention in square and round shape. The thickness of the reaction particle is designated with d.

As can be seen from the diagram of FIG. 3, the specific surface of the reaction particles exponentially decreases with thickness d of the reaction particles. The specific surface is all the greater, the smaller the thickness of the reaction particles is. An advantageous range for the specific surface (4000 to over 20,000 m²/m³) follows for thicknesses of d=0.01 mm to d=0.5 mm. For comparison, typical values for specific surfaces of usual carrier particles are indicated below:

| | |
|---|---|
| Sand (diameter = 0.7 mm): | 850 m²/m³ |
| biologically active foam cubes (edge length 1 cm): | 1000 m²/m³ |
| trickling filter material: | 100–300 m²/m³. |

The reaction particles according to the invention thus exhibit a specific surface greater by a multiple than usual carrier particles.

In FIG. 4, a reaction particle is represented in cross section, which consists of two different foils in a sandwich method of construction. Inner layer 1 forms an aluminum foil with a density of 2.7 g/cm³. Two outer layers 2 and 3 are formed from polyethylene films with a density of 0.9 g/cm³. If, e.g., the polyethylene films altogether constitute a portion of 6/7 and the aluminum foil a portion of 1/7 of the entire thickness of the reaction particle, an average density of 1.15 g/cm³ is produced. In this way, in principle every desired density of the reaction particle can be set by corresponding selection of the individual layer materials and layer thicknesses.

FIG. 5 shows a cross section of a reaction particle, which consists of two outer membrane films 2 and 3 and an inner substrate film 1. The substrate film, e.g., polyhydroxybutyric acid, can interact, e.g., with the materials contained in the waste water and/or waste gas, through the membrane film.

In FIG. 6, a cross section of a reaction particle is represented, which exhibits dents 1 on the surface. Dents 1 preferably have a diameter of about 0.05 to about 0.5 and a depth of up to 0.5 mm.

I claim:

1. A process for treating a fluid comprising:

bringing said fluid into contact with reaction particles which promote or make possible a reaction, which particles are in suspension in a reactor and/or set in motion within a reactor, wherein said fluid is drinking water, waste water, waste gas or combinations of waste water and waste gas, and wherein said reaction particles are essentially planar particles having a thickness of 5 µm–1500 µm and an area of 5 mm²–1000 mm².

2. A process according to claim 1, wherein said reaction particles have a thickness of 15 µm–500 µm.

3. A process according to claim 1, wherein said reaction particles exhibit holes with a diameter of 10 µm–1000 µm.

4. A process according to claim 3, wherein said reaction particles exhibit 10–1000 holes/cm².

5. A process according to claim 1, wherein said reaction particles exhibit embossings on their surfaces.

6. A process according to claim 1, wherein fibers, powders or combinations thereof are applied to the surfaces of said reaction particles.

7. A process according to claim 1, wherein a nonwoven fabric is applied to the surfaces of said reaction particles.

8. A process according to claim 1, wherein the surfaces of said reaction particles are doped with a reactive dopant.

9. A process according to claim 1, wherein said reaction particles are made of plastic fabric.

10. A process according to claim 1, wherein said reaction particles are made of polyolefins.

11. A process according to claim 1, wherein said reaction particles are made of polystyrene.

12. A process according to claim 1, wherein said reaction particles are made of biodegradable bioplastics.

13. A process according to claim 1, wherein said reaction particles are made of metal foils.

14. A process according to claim 1, wherein said reactor particles are made of plastic exhibiting a specific weight of 0.8 g/cm³–1.5 g/cm³.

15. A process according to claim 1, wherein said fluid is waste water, waste gas or combinations thereof and said fluid is conducted through a fluidized bed of said reaction particles.

16. A process according to claim 1, wherein said fluid is waste water which is completely and thoroughly mixed with said reaction particles in a fluidized bed reactor.

17. A process according to claim 1, wherein a biomass is applied to said reaction particles or a spontaneous growth of biomass occurs on said reaction particles.

18. A process according to claim 8, wherein the dopant applied to the surfaces of said reaction particles is zeolite powder, activated carbon or iron.

19. A process according to claim 1, wherein the ratio of reaction particle surface area to reactor volume is 50–2000 m²/m³.

20. A process according to claim 1, wherein said reaction particles have a thickness of 0.01–0.5 mm and a specific surface of 4,000–20,000 m²/m³.

\* \* \* \* \*